United States Patent [19]
Buendia et al.

[11] Patent Number: 4,780,504
[45] Date of Patent: Oct. 25, 1988

[54] SUPPORTS USEFUL IN SOLID PHASE SYNTHESIS OF OLIGONUCLEOTIDES

[75] Inventors: Jean Buendia, Le Perreux sur Marne; Jeanine Nierat, Suresnes, both of France

[73] Assignee: Roussel Uclaf, Paris, France

[21] Appl. No.: 871,451

[22] Filed: Jun. 5, 1986

[30] Foreign Application Priority Data

Jun. 20, 1985 [FR] France ............................ 85 09382

[51] Int. Cl.⁴ ..................... C12P 19/34; C12P 19/38
[52] U.S. Cl. ............................. 525/54.11; 525/54.2; 525/326.6; 536/18.5; 556/419; 556/420; 556/421; 556/422; 564/79; 564/80; 564/82; 564/89; 564/98; 564/99; 252/62.56
[58] Field of Search ............... 525/54.11, 54.2, 326.6, 525/326.7, 327.2, 327.5; 530/333, 334; 536/22, 23, 24, 25, 26, 27, 28, 29, 18.5, 124; 514/7, 76; 252/62.51, 62.54, 62.56; 556/419, 420, 421, 426; 564/79, 80, 82, 89, 98, 99

[56] References Cited

U.S. PATENT DOCUMENTS

| | | | |
|---|---|---|---|
| 4,591,614 | 5/1986 | Miller et al. | 525/54.11 |
| 4,638,032 | 1/1987 | Benner | 525/54.11 |
| 4,659,774 | 4/1987 | Webb et al. | 525/54.2 |

Primary Examiner—John Kight
Assistant Examiner—Nathan M. Nutter
Attorney, Agent, or Firm—Bierman & Muserlian

[57] ABSTRACT

Novel supports useful in solid phase synthesis of oligonucleotides of the formula

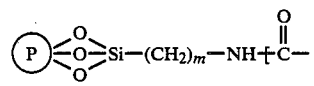

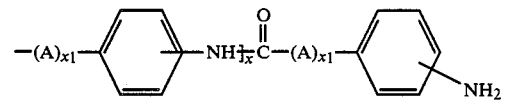

wherein $p$ is micro pellets of a material selected from the group consisting of glass, silica, Kieselguhr, polytetrafluoroethylene, cellulose and metallic oxides, m is an integer from 1 to 20, A is selected from the group consisting of alkylene of 1 to 20 carbon atoms, saturated cycloalkylene of 3 to 12 carbon atoms, phenyl and 5 to 6 member heterocycles, x is an integer from 0 to 20, $x_1$ is an integer from 0 to 10 and the amino group may be in the m-, p- or o-position, a process for the preparation of said supports, the use of said supports and intermediates.

10 Claims, No Drawings

SUPPORTS USEFUL IN SOLID PHASE SYNTHESIS OF OLIGONUCLEOTIDES

STATE OF THE ART

Many supports useful in the synthesis of oligonucleotides in the solid phase have been described in the literature. Examples of these supports are polymers such as polystyrene described in Nucleic. Ac. Res., Vol. 8, 1980, polyacrylamide acryloylmorpholide and polydimethylacrylamide polymerized onto kieselguhr described in Nucleic Ac. Res., Vol. 9(7), 1981, p. 1691 of the formula kieselguhr polyacrylamide

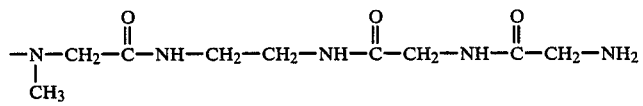

However, these supports have the disadvantage that they have a tendency to excessively swell and retain certain reactants.

Supports of an inorganic nature have also been described in the literature such as supports of the formula

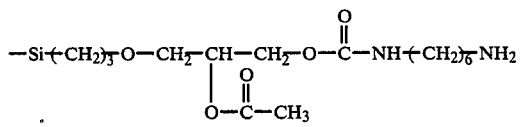

described in J.A.C.S., Vol. 105 (1983), p. 661 and silica based supports made functional by a 3-aminopropyl triethoxysilane group described in European Pat. No. 0,035,719 as being useful in the phosphite and phosphoramidite synthesis for the preparation of oligonucleotides. However, the latter support gives poor yields when used in the phosphotriester synthesis, particularly in the first couplings.

OBJECTS OF THE INVENTION

It is an object of the invention to provide novel improved supports for preparation of oligonucleotides and a process for the preparation of said supports.

It is another object of the invention to provide a novel process for the preparation of oligonucleotides and novel intermediates formed therein.

These and other objects and advantages of the invention will become obvious from the following detailed description.

THE INVENTION

The novel supports of the invention have the formula

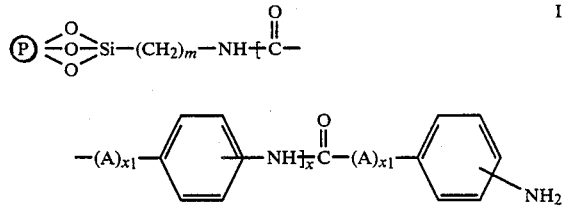

wherein Ⓟ is micropellets of a material selected from the group consisting of glass, silica, Kieselguhr, polytetrafluoroethylene, cellulose and metallic oxides, m is an integer from 1 to 20, A is selected from the group consisting of alkylene of 1 to 20 carbon atoms, saturated cycloalkylene of 3 to 12 carbon atoms, phenyl and 5 to 6 member heterocycles, x is a an integer from 0 to 20, $x_1$ is an integer from 1 to 10 and the amino group may be in the m-, p- or o-position.

Examples of A as alkyl of 1 to 20 carbon atoms are methyl, ethyl, propyl, butyl, hexyl, octyl, decyl, dodecyl and alkyl substituted with one or more methyl or ethyl groups such as methyl-1-methane-diyl; methyl-1-ethane-diyl-1,2; methyl-1 or 2-propane-diyl-1,3; methyl-1,2-propane-diyl-1,3 and ethyl-1-ethanediyl-1,2.

Examples of A as a saturated cycloalkyl are cyclopropane, cyclobutane, cyclopentane, cyclohexane, cycloheptane, cyclooctane, cyclononane, cyclodecane, cycloundecane and cyclododecane and examples of A as a heterocycle of 5 to 6 members are thiazolyl, pyridinyl, 4,5-dihydrothiazolyl, oxazolyl, isoxazolyl, imidazolyl, pyrimidyl or thienyl.

Ⓟ is preferably silica having a homogeneous particle size and the amino groups on the phenyl ring are in the m- or p-positions. A suitable commercial grade silica is Vydac A having a particle diameter of 20μ and pores of 300 Å or a chromotographic silica or HPLC silica such as Porosil B having a particle diameter of 37 to 75μ.

Preferred supports of formula I are those wherein m is an integer from 1 to 5, those wherein A is —CH₂—, more especially those wherein x is an integer from 0 to 10 and those wherein $x_1$ is an integer from 0 to 5 and m is 3.

Specific preferred supports of formula I are those having the following formulae:

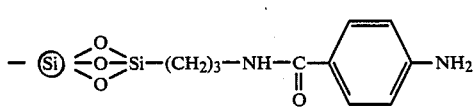

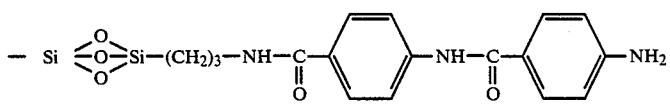

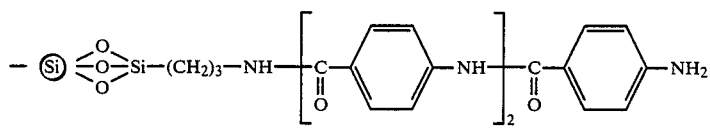

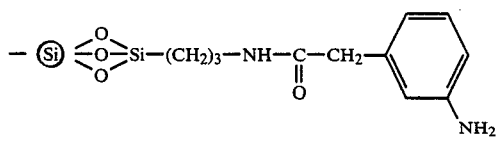

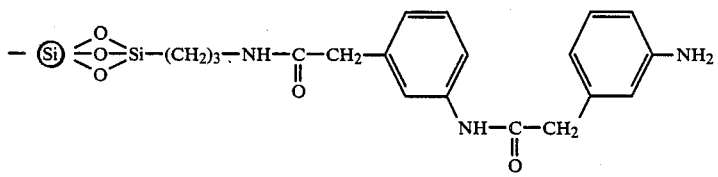

wherein Si is a silica such as Vydac A.

The novel process of the invention for the preparation of a support of formula I comprises reacting a support of the formula

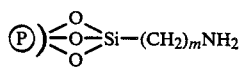

II wherein $\textcircled{P}$ and m have the above definitions with a compound of the formula

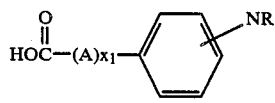

III wherein R is a protective group for a mono- or divalent amine and A and $x_1$ have the above definition in the presence of an activating agent and a tertiary base to obtain a support of the formula

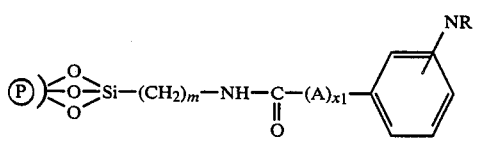

reacting the latter, depending on the nature of R, with an acid or a base to free the terminal —$NH_2$ to obtain a support of formula I in which $\textcircled{P}$, m, A and $x_1$ have the above definitions and x=0, and optionally reacting the latter with the compound of formula III under the same conditions as before to obtain an intermediate support of the formula

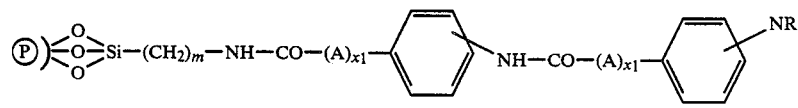

which intermediate is reacted again with an acid or a base to obtain a support of formula I in which x=1, and optionally repeating the procedure successively in this fashion passing via intermediate supports of the formula

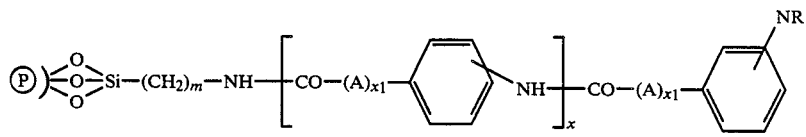

wherein R, $\textcircled{P}$, m and $x_1$ have the above definitions and x is an integer from 0 to 20 until a support of formula I wherein x is 20 is obtained.

Examples of suitable amine protective groups are an acyl of a carbonic acid such as ethoxy-carbonyl, benzyloxy-carbonyl, tert.butyloxy-carbonyl(=Boc), p-methoxy-benzyloxy-carbonyl, or fluorenylmethoxycarbonyl(=FMOC) or substituted or unsubstituted aryl or aralkyl for example benzyl or triphenylmethyl or o-nitrophenyl-sulfenyl.

When R is any of the said groups, the amine function is a secondary amine, whereas R is advantageously a stable imine and especially the grouping

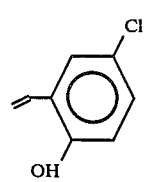

It will be understood that when R is a monovalent radical, then a hydrogen atom is attached to the nitrogen.

The process of the invention thus particularly relates to a process characterized in that R is

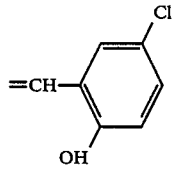

in the compound of formula III. Under the preferred conditions of the process of the invention, the activating agent employed to obtain the intermediate supports is either phenyl (phenyl phosphoramido) chloridate of the formula

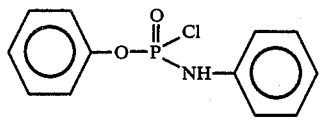

or dicyclohexylcarbodiimide and the tertiary base is preferably triethylamine or pyridine and the reaction is carried out in a solvent such as methylene chloride, dimethylformamide, tetrahydrofuran or pyridine.

The conditions for de-blocking of the terminal amine function of the intermediate supports will be adjusted according to the protective groups employed. When R is

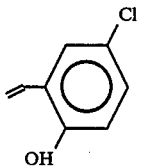

one advantageously uses hydrochloric acid or other acids such as sulfuric acid, dichloroacetic acid or trichloroacetic acid can also be employed.

The invention also has as its object the intermediate supports of the formula

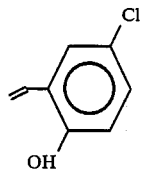

the products of formula III may be prepared as described by Sheeman et al, J. Am. C. Soc, Vol. 84, p. 2457, 1982 by the following reaction

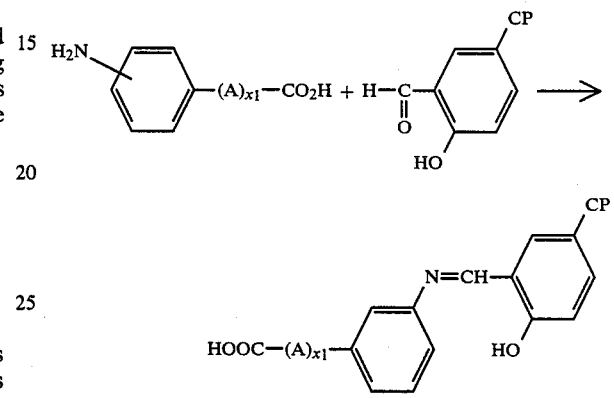

The supports of formula I permit the synthesis of oligonucleotides without difficulty in the solid phase by going through phosphoramidites, phosphites, phosphodiesters and phosphotriesters. The first nucleosides are stable intermediates and are obtained in high yields and they can be readily used in the two most classical methods of solid phase synthesis of oligonucleotides (the method going to the phosphoramidite, to the phosphite, to the phosphodiester, to the phosphotriester), as well in the 3'→5' as in the 5'→3 and for all the usual purine-type or pyrimidine-type bases. Moreover, the final hydrolysis for separating the support from the polynucleotide is achieved readily and at the same time as the deprotection of the phosphate linkages and of the protective groups for the purine-type and pyrimidine-type bases.

The invention most especially relates to the use of the supports of formula I in solid phase synthesis by the method going to the phosphotriester and the novel

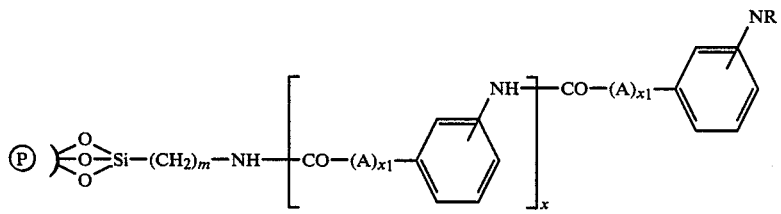

in which R, Ⓟ, m, A, x and $x_1$ are defined as above.

The supports of formula II employed as starting materials in the process of the invention are prepared as described in European Pat. No. 0,035,719. When R is desoxyribonucleosides and ribonucleosides obtained during the synthesis of oligonucleotides using the supports of formula I.

The said novel desoxyribonucleosides and ribonucleosides on supports have the formula

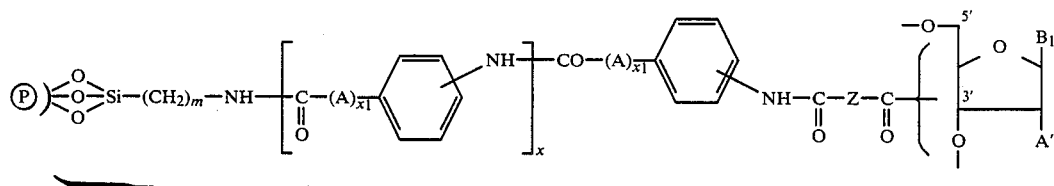

Formula I wherein the support of formual I is joined to a ribonucleoside or to a desoxyribonucleoside, either at the 3' position or at the 5' position, via the intermediary of a $$-\underset{\underset{O}{\|}}{C}-Z-\underset{\underset{O}{\|}}{C}-$$

group, Z is a hydrocarbon of 2 to 20 carbon atoms, or a phenyl, the hydroxyl being optionally protected either at the 3' position, or at the 5' position, and A' either is hydrogen if the support of formula I is joined to a desoxyribonucleoside, or is $OR_1$ if the support of formula I is bound to a ribonucleoside, $R_1$ being either hydrogen, or a conventional protective group for the hydroxyl, and $B_1$ is a purine-type or pyrimidine-type base whose amine function is optionally protected.

The preferred novel desoxyribonucleosides on support have the formula yribonucleotides or oligoribonucleotides on supports in which the nucleoside is attached either at the 3' position or at the 5' position to the support of formula I have the formula

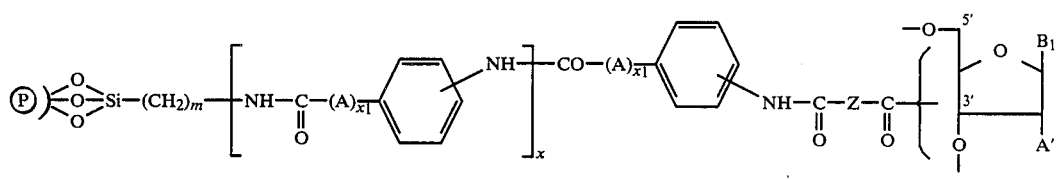

Formula I which is itself joined via phosphodiester or triester linkages of the type

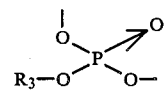

wherein $R_3$ is either hydrogen or a protective group to other nucleotides carrying the bases $B_2, \ldots B(y-1)$, as far as the last necleoside of the formula

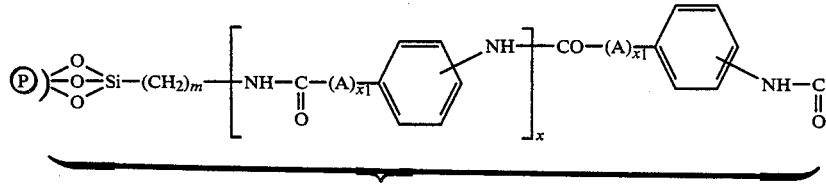

Formula I wherein the support of formula I is joined to a desoxyribonucleoside at the 3' position via the intermediary of

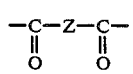

wherein Z is a hydrocarbon of 2 to 20 carbon atoms or phenyl and the hydroxyl function at 5' is optionally protected by a conventional protective group $R_2$, and $B_1$ is a purine-type or pyrimidine-type base whose amine function is optionally protected. The novel oligodesox- By being the last base of the oligodesoxy- or oligoribonucleotide, the hydroxyl of the last nucleoside at 5' or at 3' being optionally protected, and the various purine-type or pyrimidine-type bases having their amine functions possibly protected.

The preferred novel oligodesoxyribonucleotides on supports have the formula

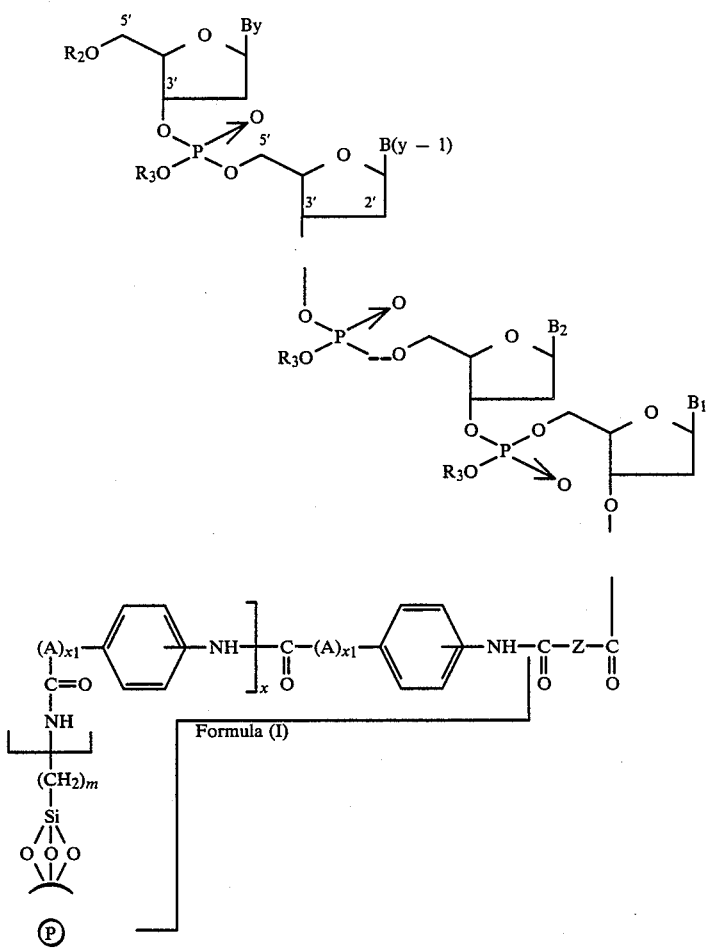

wherein the support of formula I is joined at 3' to an oligodesoxyribonucleotide carrying the bases $B_1$, $B_2$ - - - $B_y$, and $R_2$ is either hydrogen or a protective group, $R_3$ is either hydrogen or a protective group, the purine-type or pyrimidine-type bases possibly having their amine functions protected.

In the desoxyribonucleosides, ribonucleosides, oligodesoxyribonucleotides or oligoribonucleotides on the supports hereinbefore defined, Z is preferably phenyl or —$(CH_2)_n$—, n being an integer of 2 to 20, most preferably Z is —$(CH_2)_2$—. In the ribonucleosides or oligoribonucleosides, $R_1$ is a conventional protective group for the hydroxyl such as a pyranyl, silyl or benzyl.

In the nucleosides or nucleotides, the bases $B_1$, $B_2$ - - - $B_y$ may be adenine, guanine (purine type bases), cytosine, uracyl or thymine (pyrimidine type bases). These bases can also be substituted purine or pyrimidine-type bases such as for example 6-methylaminopurine or 6-dimethylaminopurine, 1-methyl-guanine, 5-methyl-cytosine, 5-hydroxymethyl-cytosine or dihydro-uracil. All the so-called rare or minor bases found in certain nucleic acids can be employed.

The protective groups for the amine functions of these bases are for example benzoyl or isobutyryl. The protective $R_2$ for the hydroxyl function at 5' is for example, trityl, monomethoxytrityl, dimethoxytrityl or pixyl.

The protective $R_3$ for the hydroxyls of the phosphate group is for example ortho or para chlorophenyl.

The methods for the synthesis of the oligonucleotides mentioned above are very conventional and well known to the man in the art and are summarized for example in the article The Chemical Synthesis of DNA, Aldrichimica Acta, Vol. 16, No. 3-1983.

The different stages in the 3'→5' synthesis of oligodesoxyribonucleotides by the method going to the phosphotriesters are briefly summarized hereinafter and the stages are exactly the same for the synthesis of oligoribonucleotides and/or if the synthesis proceeds from 5'→3', the protective group for the hydroxy at the 3' position need in this case to be appropriately chosen.

1. Preparation of an activated desoxynucleoside:

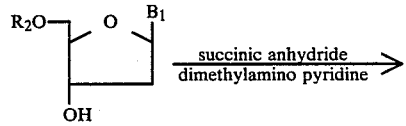

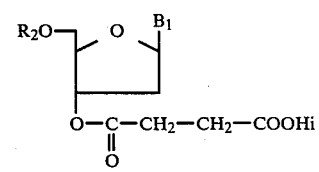

The acid may either be free or activated by a pentachlorophenyl (Itakura et al. Nucl. Ac. Res. 8, 22, 5473, 1980) or by a p-nitrophenyl: (M. H. Caruther, Chemical and Enzymatic Synthesis of Gene Fragments, H. Cr. Gassen and A. Lang, Verlag Chemie (1982) p. 71).

2. Condensation of the desoxynucleoside prepared above upon a support of formula I schematically denoted hereinafter as

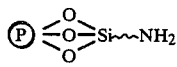
I

This condensation takes place in solution in dimethylformamide employing as catalyst either triethylamine for 20 to 24 hours, or dicyclohexycarbodiimide in pyridine (1 night to 3 days), or 4-dimethylamino-pyridine in pyridine to obtain a compound of the formula The hydroxyl at the 5' position may be freed by treatment with a Lewis acid, for example with zinc bromide or with di- or trichloroacetic acid.

3. Extension of the desoxyoligonucleotide chain:

Either monomeric nucleotides or dimeric nucleotides in the form of their triethyl ammonium salts may be used and the dimers are stocked in the form of cyanoethyl derivatives. The triethylammonium salts are prepared immediately before the synthesis.

After eliminating the protective group for the 5' hydroxyl of the first nucleoside fixed upon the support, this dimer is condensed in the presence of mesitylsulfonyl 3-nitro-1,2,4-triazole or MSNT, or in the presence of a mixture of mesitysulfonyl chloride and methyl imidazole in pyridine to obtain a compound of the formula

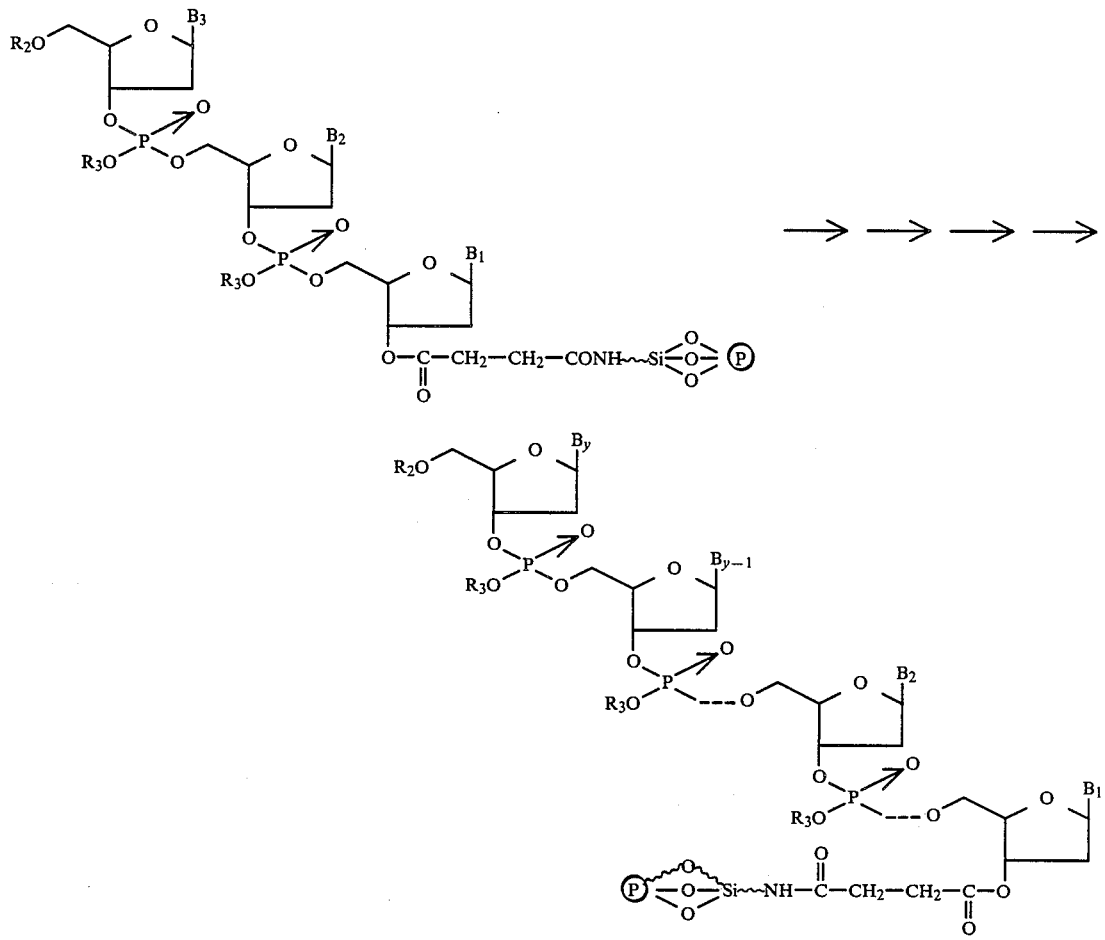

After each link-up, the protective group at 5' of the last nucleotide attached to the chain is eliminated.

4. Separation of the support and the oligonucleotide chain

For example, a mixture of p-nitrobenzaldoxime and N,N,N',N'-tetramethylguanidine in a mixture of dioxane and water (1/1) are used to detach the oligonucleotide from the support. This very weak reagent also makes it possible to selectively cleave the arylic phosphate linkages in relation with aliphatic phosphates, thus achieving the de-blocking of the phosphates without breaking the synthesized chain. It is then necessary to treat the oligonucleotide thus obtained in such a way as to liberate all the functions protected during the synthesis. Several purification treatments (HPLC electrophoresis) are then necessary to obtain the desired polynucleotide.

One final stage of the sequence of operations will alone make it possible to know with certainly the structure of the oligonucleotide, if that seems necessary.

The supports of formula I of the invention can equally be used in peptidic synthesis.

In the following examples there are described several preferred embodiments to illustrate the invention. However, it is to be understood that the invention is not intended to be limited to the specific embodiments.

EXAMPLE 1

Preparation of the support of the formula

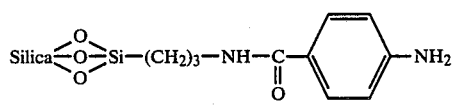

STEP A: Preparation of the support starting material of the formula

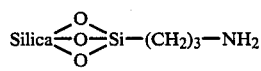

Using the procedure of Example 1 of European Pat. No. 0,035,719, 10 g of Vydac A silica with a particle size of 20μ and 300 Å pores and 11.5 g of 3-aminopropyltriethoxy silane were reacted to obtain the above support with a —NH₂ titer of $3 \times 10^{-4}$ equivalent per gram (estimated by picrid acid method).

STEP B: 4-[(5-chloro-2-hydroxy-benzylidene)-aminol]-benzoic acid

Using the procedure of Sheeman et al [J.A.C.S., Vol. 84 (1982), p. 2457], 1.37 g of p-amino-benzoic acid, 2.35 g of 5-chlorosalicylaldehyde, 240 ml of ethanol and 17 ml of anhydrous methanol were reacted to obtain 2.59 g of 4-[(5-chloro-2-hydroxy-benzylidene)amino]-benzoic acid.

STEP C: Phenyl (phenylphosphoramido)-chloridate

Using the procedure of Synthesis, 288 (1982), 22.3 ml of phenyl phosphorodichloridate, 175 ml of anhydrous benzene and a solution of 12.5 ml of aniline in 25 ml of anhydrous benzene were reacted to obtain 24.8 g of phenyl (phenylphosphoramido)-chloridate STEP D: Support preparation A mixture of 600 mg of the support of Step A, 550 mg of the product of Step B, 534 mg of the product of Step C, 10 ml of methylene chloride and 0.54 ml of triethylamine was stirred overnight and was then vacuum filtered. The product was empasted with dimethylformamide at 100° C. until the filtrate was colorless. A ninhydrin test on the silica was negative which indicated the absence of free amino groups. 583 mg of the support were suspended in 5 ml of a 1-1 methanol-water mixture and 0.1N hydrochloric acid was added to keep the pH at 1 while stirring for one hour. The mixture was vacuum filtered and the product was successively washed with 20 ml of a 1-1 methanol-water mixture, 100 ml of anhydrous methanol and 100 ml of methylene chloride and was then dried under reduced pressure overnight to obtain 563.5 mg of the desired support.

EXAMPLE 2

Preparation of the support

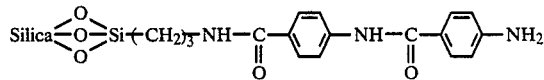

Using the procedure of Step D of Example 1, the support of Example 1 was reacted to obtain 490 mg of the above support having an —NH₂ titre of $2 \times 10^{-4}$ equivalent per gram by the picric acid test.

EXAMPLE 3

Using the procedure of Step D of Example 1, the support of Example 2 was reacted to obtain 462 mg of the support of the formula

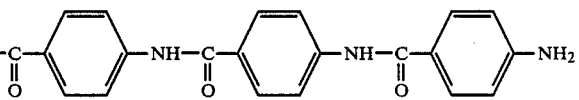

having an —NH₂ titre of $1.5 \times 10^{-4}$ equivalent per gram by the picric acid method.

EXAMPLE 4

STEP A: 3-[(5-chloro-2-hydroxy-benzylidene)-amino]-phenylacetic acid

Using the procedure of Sheeman et al [J.A.C.S., Vol. 84, (1982), p. 2457], 1.5 g of 3-amino-phenylacetic acid, 1.72 g of 5-chloro-2-hydroxy-benzaldehyde, 480 ml of 100% ethanol and 35 ml of methanol were reacted to obtain 2 g of 3-[(5-chloro-2-hydroxy-benzylidene)-amino]-phenylacetic acid.

STEP B: Preparation of the support

A mixture of 200 mg of the support of Step A of Example 1, 5 ml of anhydrous pyridine, 275 mg of the product of Step A and 200 mg of dicyclohexyl carbodiimide was stirred at room temperature for 48 hours and was then vacuum filtered. The product was successively washed with dioxane, methanol, hot dimethylformamide and methanol and was then dried under reduced pressure at room temperature to obtain 195 mg of the expected support with a negative nihydrin test.

The previously obtained silica was suspended in 2 ml of 0.1N hydrochloric acid, 5 ml of methanol and 3 ml of water and the suspension was stirred for one hour at room temperature. The mixture was vacuum filtered and the product was washed with a 1-1 water-methanol mixture to obtain 190 mg of the support of the formula

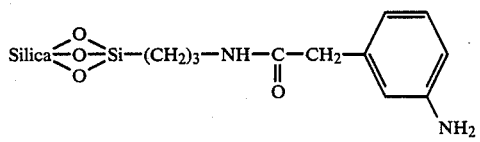

with an —NH₂ titre of $1.95 \times 10^{-4}$ equivalent per grams (by photometric estimation under UV light of free 2-hydroxy-5-chloro-benzaldehyde in the filtrate).

EXAMPLE 5

A mixture of the support of Example 4, 5 ml of anhydrous pyridine, 200 mg of 3-[(5-chloro-2-hydroxy-benzylidene)-amino]phenylacetic acid and 200 mg of dicyclohexylcarbodiimide was stirred for 72 hours and was then vacuum filtered. The product was successively washed with dimethylformamide, methanol, methylene chloride and ether and was dried under reduced pressure. A mixture of the product, 5 ml of methanol, 3 ml of water and 2 ml of 0.1N hydrochloric acid was stirred for one hour and was vacuum filtered. The product was washed with a 1-1 water-methanol mixture to obtain 180 mg of the support of the formula

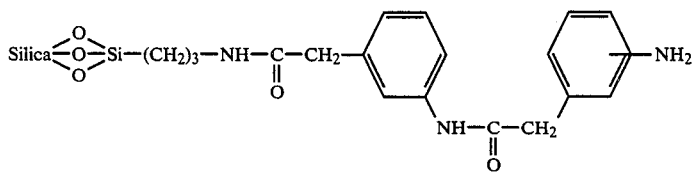

having an $-NH_2$ titre of $1.97 \times 10^{-4}$ equivalent per gram (test method of Example 4).

EXAMPLE 6

Synthesis of oligonucleotides by the phosphotriester method

The support of formula I was placed in a minicolumn between two polyfluoroethylene filters and the two filters were kept in a fixed position by two hollow pistons. The assembly was closed at the top by a screw-stopper provided with a septum through which by means of a syringe one introduced the mixture for coupling. The apparatus employed is comparable to that described in Chemical and Enzymatic Synthesis of Gene Fragments, H. Cr. Gassen A. Lang, Verlag Chemie 82, p. 14. All the repetitive operations of washing and introducing the reactants were automated and the number of nucleotides to be introduced for the overall synthesis was programmed. The introduction of the nucleotide was the only manual operation which had to be effected by the syringe.

25 to 150 mg quantities of the support of formula I were condensed with the first nucleoside carrying the first base $B_1$ which was necessary for the synthesis envisaged into the reaction vessel. One appropriately programed the desired parameters, in particular the number of nucleotides to be attached, then the following automatic cycle was started as indicated in the following Table.

STEP 1:

| Solvent | Manner of Introduction | Time |
|---|---|---|
| Pyridine | Continuous flow 1 cm3/mn | 5 mn |
| 10% Solution of phenyl isocyanate in pyridine | Programed fractions | 10 mn |
| Pyridine | Continuous flow 1 cm3/mn | 5 mn |
| Methylene chloride | Continuous flow about 2 cm3/mn | 3 mn |
| 10% Solution of dichloro acetic acid in methylene chloride | Continuous flow about 2 cm3/mn | 4.5 mn |
| DMF | Continuous flow | 5 mn |

-continued

| Solvent | Manner of Introduction | Time |
|---|---|---|
| Pyridine | about 1 cm3/mn Continuous flow about 1 cm3/mn | 5 mn |
| Mixture to be coupled | By syringe | 15 mn to 1 h |

STEP 2:

As many cycles identical to the first one were carried out as was necessary to obtain the desired nucleotide. The solvents employed in this cycle of synthesis were very pure and anhydrous. UV estimation of the quantity of trityl ions after detritylation made it possible to know the yield of each coupling. The mixture to be coupled was prepared immediately before use, and comprised 10 equivalents of the triethylammonium salts of the monomeric or dimeric nucleotide (relative to the quantity of the first nucleoside present on the solid support); and 30 equivalents of mesityl sulfonyl 3-nitro 1,2,4-triazole or MSNT, in anhydrous pyridine (0.3 ml per about 50 mg of dimer). This mixture was transferred into a syringe under an atmosphere of anhydrous argon and was introduced in three repetitive batches at regular intervals.

To obtain the wholly-deprotected oligonucleotides, it was then necessary to carry out a certain number of treatments which are fully conventional and described for example in Chemical and Enzymatic Synthesis of Gene Fragments, H. Cr. Gassen and A. Lang, Verlag Chemie 82, pages 2 to 42.

These treatment were as follows:

(1) Cleaving the nucleotide from its solid support

One effected treatment with a 0.3M solution of 1,1,3,3-tetramethyl guanidinium o-nitrobenzaladoximate in a dioxane-water (1-1) mixture and then proceeded in the fully-conventional manner described in Nucleic Acids Research, Vol. 9 No. 18 1981, p. 4611. This very weak reactant also enabled selective cleavage of the arylic phosphate linkages in relation with aliphatic phosphates, thus achieving the de-blocking of the phosphates without breaking the synthesized chain.

(2) De-blocking the amine functions of the nitrogen bases

Treatment with saturated ($\simeq$37%) $NH_4OH$ liberated all the amines in the nitrogen bases.

(3) De-blocking of the function at 5' in the last nucleotide

Treatment was with a $CH_3COOH$-water (4-1) mixture and after concentration to dryness under reduced pressure, the product was taken up in water, extracted with ether to eliminate all the reactants and the cleavage products. The oligonucleotide with y chain links thus contained numerous impurities (nucleotides with y-2, y-4 - - - chain links, the products of various degradations). To obtain the desired product required several successive stages of purification: namely chromatography over gels, HPLC, electrophoresis and sequencing. This last-mentioned procedure revealed the sequence of monomeric nucleotides without ambiguity and in order. These procedures are fully conventional.

EXAMPLE 7

Oligodesoxyribonucleotides synthesized employing the support of Example 2

(1) Preparation of 5'-dimethoxytrityol 2'-desoxy-thymidine 3'-p-nitrophenyl succinate Using the method described by Caruthers, Chemical and Enzymetic Synthesis of Gene Fragments, H. Cr. Gassen and A. Lang, Verlag Chemie (1982) p. 71, 1.557 g of 5'-dimethoxytrityl-2'-desoxythymidine-3'-succinic acid, 10 ml of anhydrous dioxane, 0.5 ml of anhydrous pyridine, 369 mg of p-nitrophenol and 585 mg of dicyclohexyl carbodiimide in solution in 2.5 ml of anhydrous dioxane were reacted to obtain 1.150 g of 5'dimethyloxytrityl 2'-desoxy thymidine 3'-p-nitrophenyl succinate.

(2) Condensation between the support of Example 2 and the activated thymidine succinate A mixture of 99 mg of the support of Example 2 titrating $2 \times 10^{-4}$ eq/g of $NH_2$ and 80 mg of the activated thymidine succinate of Step 1, being about 6.3 equivalents, and 80 mg of dicyclohexyl carbodiimide and 2 ml of pyridine was stirred in the dark for 72 hours and was then vacuum filtered. The product was washed successively with pyridine, with a mixture of methylene chloride and methanol, and with methylene chloride and then dried under reduced pressure to obtained 95 mg of the expected condensed support having a dimethoxytrityl titre of $8.8 \times 10^{-5}$ eq/g.

Starting from the support condensed with thymidine succinate, when using three monomers the oligodesoxyribonucleotide 5'-d (T C T A) was obtained and when using three dimers, the oligodesoxyribonucleotide 5'-d (TCC TT AC) was obtained.

EXAMPLE 8

Oligodesoxyribonucleotide synthesised with the support of Example 3

STEP A: Preparation of 5'-dimethoxytrityl-2'-N benzoyl-desoxycytidine-3'-p-nitro-phenyl succinate Using the method of Caruthers, Chemical and Enzymatic Synthesis of Gene Fragments, H-Cr Gassen and A. Lang, Verlag Chemie (1982) p. 71, 4.16 g of 5'-dimethoxytrityl-2'-desoxy-N-benzoyl-cytidine-3'-succinic acid, 25 ml of anhydrous dioxane, 0.8 ml of pyridine, 1.16 g of p-nitrophenol, and 1.83 g of dicyclohexylcarbodiimide in 8.33 ml of pyridine were reacted to obtain 3.6 of 5'-dimethoxytrityl-2'-N benzoyl-desoxycytidine-3'-p-nitro-phenyl succinate.

STEP B: Condensation between the support of Example 3 and the activated cytosine succinate For two days in darkness, a mixture of 100 mg of the support of Example 3 titrating $1.5 \times 10^{-4}$ eq/g of $NH_2$ and 110 mg of the activated cytosine succinate of Step A, being about 10 equivalents, and 87 mg of dicyclohexylcarbodiimide were stirred and filtered. The product was washed and dried as in Example 7 to obtain 95 mg of the expected condensed support having a dimethoxytrityl titre of $7 \times 10^{-5}$ eq/g.

Starting from the support condensed with the cytosine succinate and using 3 dimers, the oligodesoxyribonucleotide 5'-d (CCC TTAC) was obtained.

EXAMPLE 9

Oligo desoxyribonucleotides synthesised with the support of Example 5

145 mg of the support of Example 5 were condensed with 220 mg of the activated cytosine succinate in the presence of 150 mg of dicyclohexylcarbodiimide and 2 ml of pyridine in the same manner as in Example 8 to obtain 140 mg of the expected condensed support titrating $5.55 \times 10^{-5}$ eq/g dimethoxytrityl.

Starting from this condensed support and using 3 dimers, the oligodesoxyribonucleotide 5'-d (CCC TTAC) was obtained and when employing two dimers, one obtains the oligodesoxyribonucleotide 5'-d (CCCTT).

Various modifications of the products and methods of the invention may be made without departing from the spirit or scope thereof and it should be understood that the invention is intended to be limited only as defined in the appended claims.

What we claim is:

1. A support of the formula

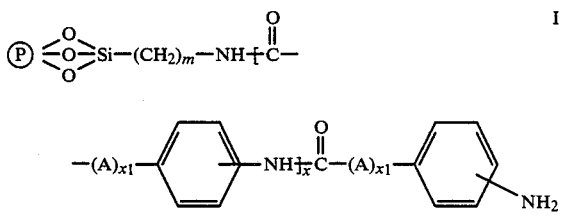

wherein (P) is micropellets of a material selected from the group consisting of glass, silica, Kieselguhr, polytetrafluoroethylene, cellulose and metallic oxides, m is an integer from 1 to 20, A is selected from the group consisting of alkylene of 1 to 20 carbon atoms, saturated cycloalkylene of 3 to 12 carbon atoms, phenyl and 5 to 6 member heterocycles, x is an integer from 0 to 20, $x_1$ is an integer from 0 to 10 and the amino group may be in the m-, p- or o-position.

2. A support of claim 1 wherein (P) is a silica material having a homogeneous particle size and the amine groups on the phenyl are in the meta- or para-position.

3. A support of claim 1 wherein m is an integer from 1 to 5.

4. A support of claim 1 wherein A is $-CH_2-$.

5. A support of claim 1 wherein x is an integer from 0 to 10 and $x_1$ is an integer from 0 to 5.

6. A support of claim 1 wherein m is 3.

7. A support of claim 1 selected from the group consisting of

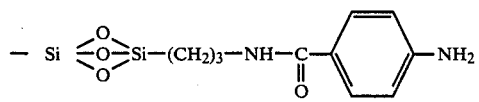

-continued

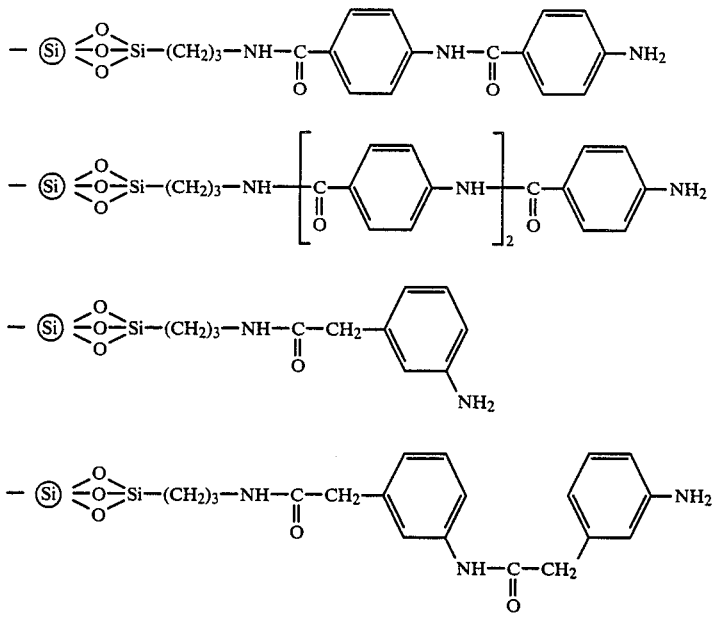

wherein Si is Vydac A silica.

8. A process for the preparation of a support of claim 1 comprising reacting a support of the formula

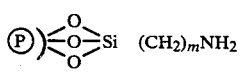

II wherein ⓟ and m have the above definitions with a compound of the formula

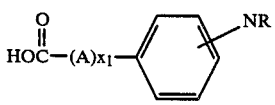

III

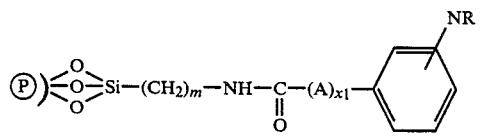

wherein R is a protective group for a mono- or divalent amine and A and $x_1$ have the above definitions in the presence of an activating agent and a tertiary base to obtain a support of the formula reacting the latter, depending on the nature of R, with an acid or a base to free the terminal —$NH_2$— to obtain a support of formula I in which ⓟ, m, A and $x_1$ have the above definitions and x=0, and optionally reacting the latter with the compound of formula III under the same conditions as before to obtain an intermediate support of the formula

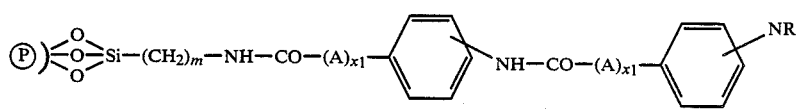

which intermediate is reacted again with an acid or a base to obtain a support of formula I in which x=1, and optionally repeating the procedure successively in this fashion passing via intermediate supports of the formula

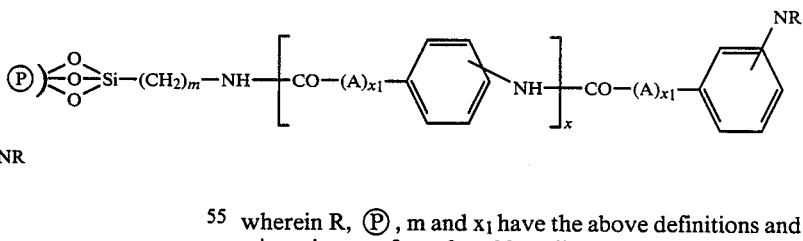

wherein R, ⓟ, m and $x_1$ have the above definitions and x is an integer from 0 to 20 until a support of formula I wherein x is 20 is obtained.

9. The process of claim 8 wherein R is

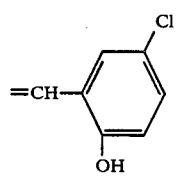

10. An intermediate support of the formula

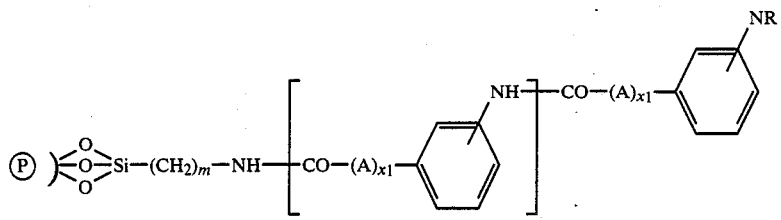

wherein Ⓟ is micro pellets of a material selected from the group consisting of glass, silica, Kieselguhr, polytetrafluoroethylene, cellulose and metallic oxides, m is an integer from 1 to 20, A is selected from the group consisting of alkylene 1 to 20 carbon atoms, saturated cycloalkylene of 3 to 12 carbon atoms, phenyl and 5 to 6 member heterocycles, $x_1$ is an integer from 0 to 10 and R is a protective group for a mono-or divalent amine.

* * * * *